United States Patent

Clément et al.

[11] Patent Number: 6,111,083
[45] Date of Patent: Aug. 29, 2000

[54] DISPERSE DYES

[75] Inventors: Antoine Clément; Alfons Arquint, both of Basel; Urs Lauk, Zürich, all of Switzerland

[73] Assignee: Ciba Specialty Chemicals Corporation, Tarrytown, N.Y.

[21] Appl. No.: 09/294,481

[22] Filed: Apr. 20, 1999

[30] Foreign Application Priority Data

Apr. 23, 1998 [EP] European Pat. Off. ............. 98810359

[51] Int. Cl.⁷ .............. C09B 29/085; D06P 3/54; C07C 233/43
[52] U.S. Cl. ............. 534/854; 534/581; 560/43; 8/693; 8/922
[58] Field of Search ............... 534/854; 560/43; 8/693, 922

[56] References Cited

U.S. PATENT DOCUMENTS

| | | | |
|---|---|---|---|
| 2,373,700 | 4/1945 | NcNally et al. | 534/852 |
| 3,406,165 | 10/1968 | Kruckenberg | 534/854 |
| 5,550,217 | 8/1996 | Trottmann | 534/732 |
| 5,723,587 | 3/1998 | Clément et al. | 534/854 |
| 5,869,628 | 2/1999 | Herzig et al. | 534/854 |
| 5,939,579 | 8/1999 | Herzig et al. | 560/43 |
| 5,942,604 | 8/1999 | Herzig et al. | 534/854 X |

FOREIGN PATENT DOCUMENTS 1012238  12/1965  United Kingdom .

*Primary Examiner*—Fiona T. Powers
*Attorney, Agent, or Firm*—Kevin T. Mansfield

[57] ABSTRACT

Disperse dyes of formula

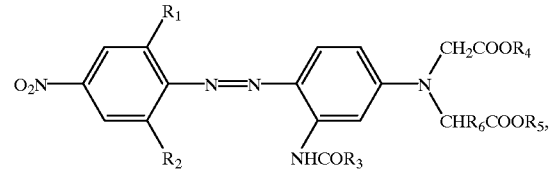

(1)

wherein $R_1$ is nitro or cyano, $R_2$ is halogen, $R_3$ is $C_1$–$C_4$alkyl, $R_4$ and $R_5$ are each independently of the other methyl or ethyl and $R_6$ is hydrogen, methyl or ethyl, with the proviso that $R_6$ is not hydrogen if $R_1$ is cyano, $R_2$ is halogen and $R_3$ is methyl or isopropyl or if $R_1$ is nitro, $R_2$ is halogen and $R_3$ is methyl.

These dyes are suitable in particular for dyeing and printing polyester textile materials.

12 Claims, No Drawings

DISPERSE DYES

The present invention relates to disperse dyes, to a process for their preparation and to their use for dyeing or printing semisynthetic or synthetic hydrophobic fibre materials.

Disperse dyes, i.e. dyes which contain no water solubilising groups, have been known for a long time and are used for dyeing hydrophobic textile materials. However, the dyeings obtained are often not sufficiently fast to thermomigration and some have also unsatisfactory fastness properties, in particular fastness to washing and perspiration. This problem occurs especially in the case of red to blue shades.

This invention relates to disperse dyes giving dyeings which are very fast to thermomigration as well as to washing and perspiration and which furthermore possess good build-up properties both in the exhaust and in the thermosol process and in textile printing. The dyes are also suitable for discharge printing.

The dyes of this invention conform to formula

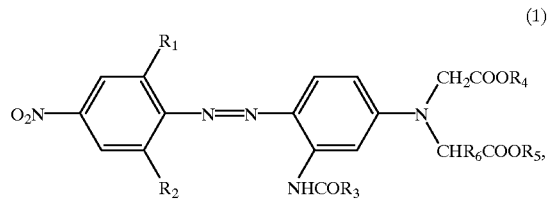
(1)

wherein $R_1$ is nitro or cyano, $R_2$ is halogen, $R_3$ is $C_1$–$C_4$alkyl, $R_4$ and $R_5$ are each independently of the other methyl or ethyl, and $R_6$ is hydrogen, methyl or ethyl, with the proviso that $R_6$ is not hydrogen if $R_1$ is cyano, $R_2$ is halogen and $R_3$ is methyl or isopropyl or if $R_1$ is nitro, $R_2$ is halogen and $R_3$ is methyl.

$R_2$ defined as halogen is typically chloro, bromo or iodo.

$R_3$ defined as $C_1$–$C_4$alkyl is, for example, methyl, ethyl, n-propyl, isopropyl, n-butyl, sec-butyl, tert-butyl or isobutyl.

$R_2$ is preferably chloro or bromo and, most preferably, bromo.

$R_3$ is preferably $C_1$–$C_3$alkyl, more preferably methyl, ethyl or isopropyl. $R_3$ is particularly preferably methyl or ethyl and, most preferably, methyl.

$R_6$ is preferably methyl or ethyl and, most preferably, methyl.

Preferred dyes of formula (1) are those, wherein $R_1$ is cyano, $R_2$ is chloro or bromo, $R_3$ is $C_1$–$C_3$alkyl, preferably methyl or ethyl and, very particularly preferably, methyl, $R_4$ and $R_5$ are each independently of the other methyl or ethyl, more preferably methyl, and $R_6$ is methyl.

The dyes of formula (1) can be prepared by processes which are known per se. They are obtained, for example, by diazotising a compound of formula

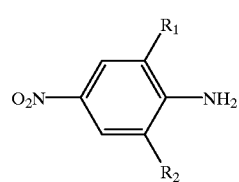
(2)

and coupling the diazonium compound so obtained to a coupling component of formula

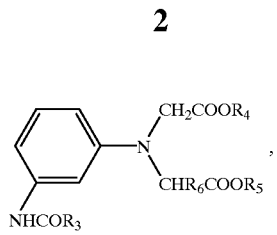
(3)

wherein $R_1$, $R_2$, $R_3$, $R_4$, $R_5$ and $R_6$ have the meanings cited for formula (1).

The diazotisation of the compounds of formula (2) is carried out in a manner known per se, for example using sodium nitrite in acid, e.g. hydrochloric or sulfuric, aqueous medium. The diazotisation can also be carried out using other diazotisation agents, for example nitrosylsulfuric acid. An additional acid may be present in the reaction medium during diazotisation, for example phosphoric acid, sulfuric acid, acetic acid, propionic acid, hydrochloric acid or mixtures of these acids, e.g. mixtures of phosphoric acid and acetic acid. Diazotisation is conveniently carried out in the temperature range from −10 to 30° C., preferably from −10° C. to room temperature.

Coupling of the diazotised compound of formula (2) to the coupling component of formula (3) is also carried out in known manner, for example in acid, aqueous or aqueous-organic medium, preferably in the temperature range from −10 to 30° C., more preferably below 10° C. Acids used are, for example, hydrochloric acid, acetic acid, sulfuric acid or phosphoric acid. Diazotisation and coupling can, for example, be carried out in the same reaction medium.

Some of the diazo components of formula (2) and the coupling components of formula (3) are known or can be prepared in a manner known per se.

The coupling component of formula

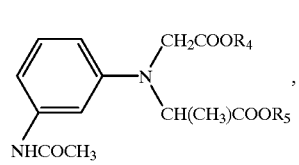
(3a)

wherein $R_4$ and $R_5$ are as defined for formula (1), is novel and is another subject matter of this invention.

The coupling component of formula (3a) is prepared, for example, by reacting 3-aminoacetanilide first with a compound of formula $CH_3$—$CHCl$—$COOR_5$ and then with a compound of formula $Cl$—$CH_2$—$COOR_4$.

The novel dyes of formula (1) can be used for dyeing and printing semisynthetic and, preferably, synthetic hydrophobic fibre materials, especially textile materials. Textile materials consisting of blended fabrics containing such semisynthetic or synthetic hydrophobic fibre materials can also be dyed or printed by means of the dyes of this invention.

Suitable semisynthetic textile materials are mainly cellulose-2½ acetate and cellulose triacetate.

Synthetic hydrophobic textile materials consist mainly of linear aromatic polyesters, for example of those consisting of terephthalic acid and glycols, in particular ethylene glycol or condensates of terephthalic acid and 1,4-bis(hydroxymethyl)cyclohexane; of polycarbonates, e.g. those consisting of α,α-dimethyl-4,4'-dihydroxydiphenylmethane and phosgene, and of fibres based on polyvinyl chloride and polyamide.

The novel dyes are applied by known dyeing processes. Polyester fibre materials, for example, are dyed by the exhaust process from an aqueous dispersion in the presence of conventional anionic or non-ionic dispersants and, where appropriate, in the presence of customary carriers, in the temperature range from 80 to 140° C. Cellulose-2½ acetate is preferably dyed at a temperature from about 65 to 85° C. and cellulose triacetate at temperatures of up to 115° C.

The novel dyes do not, or only to a minor extent, dye wool and cotton present at the same time in the dye bath (very good reserve) so that they are also very useful for dyeing polyester/wool and polyester/cellulose fibre blends.

The novel dyes are suitable for dyeing by the thermosol process, in the exhaust and continuous process and for printing processes. The exhaust process is preferred. The liquor ratio depends on the apparatus used, on the substrate and on the form of presentation. However, this ratio can be chosen from within a wide range, for example from 1:4 to 1:100, and is preferably from 1:6 to 1:25.

The cited textile material can be in various forms of presentation, for example in the form of fibres, threads or bonded fibre fabric, wovens or knits.

It is advantageous to convert the novel dyes prior to use to a dye formulation. To this purpose the dye is ground so that its particle size is on average from 0.1 to 10 micron. Grinding can be carried out in the presence of dispersants. The dried dye is ground, for example, with a dispersant or is kneaded in paste form with a dispersant and then dried under vacuum or by spraying. After adding water, the formulations so obtained can be used to prepare printing pastes and dye baths.

For printing, the customary thickeners are used, for example modified or non-modified natural products, for example alginates, British gum, gum arabic, crystal gum, carob bean flour, tragacanth, carboxymethyl cellulose, hydroxyethyl cellulose, starch, or synthetic products, for example polyacrylamides, polyacrylic acid or their copolymers, or polyvinyl alcohols.

The dyes of this invention are resistant to iron ions and copper ions and provide the cited materials with level shades having very good fastness properties, such as good fastness to light and sublimation. The excellent fastness to washing and perspiration of the dyeings obtained is to be highlighted, especially their good fastness to thermomigration. The novel dyes are also distinguished by good exhaustion and build-up.

The novel dyes are also very useful for preparing mixed shades, together with each other and also together with other dyes.

This invention relates both to the above uses of the novel dyes and to a process for dyeing or printing semisynthetic or synthetic hydrophobic fibre material, in particular textile material, which process comprises applying one or several novel dyes to the cited material or incorporating them therein. The cited hydrophobic fibre material is preferably textile polyester material. Other substrates which can be treated by the novel process and preferred process conditions are to be found above in the detailed description of the use of the novel dyes.

The novel dyes of formula (1) are also suitable for modern recording processes, for example thermotransfer printing.

The following Examples illustrate the invention in more detail. Unless otherwise stated, parts and percentages are by weight. The temperatures are given in degrees Celsius. The relationship between parts by weight and parts by volume is the same as that between the gramme and the cubic centimeter.

EXAMPLE 1

50.0 parts of 3-aminoacetanilide are added at a temperature of 20 to 30° C. to 200 parts of methyl 2-chloropropionate in a reaction flask. Subsequently, 66 parts of sodium carbonate are added. With continuous stirring, the resulting suspension is evenly heated to 127° C. and is kept at this temperature for 5 hours. Excess methyl 2-chloropropionate is then removed by distillation under vacuum at 125° C. 120 parts of methyl chloroacetate are then added to the reaction mixture which is then kept at 115° C. for 8 hours. The reacted mixture is then cooled to room temperature, charged with 330 parts of water and stirred for 30 minutes until the salts are completely dissolved. After the mixture is left standing for a short while, 2 phases form in the reaction flask. The lower, organic phase is separated. In a rotary evaporator, excess methyl chloroacetate is removed by distillation from the organic phase. The resulting 105 parts of the compound of formula

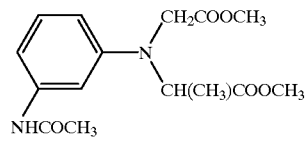

(100)

in the form of a resinous residue are dissolved in 195 parts of acetic acid.

EXAMPLE 2

In a reaction flask, 78.6 parts of 2-bromo-4,6-dinitroaniline are dissolved in 107 parts of 98% sulfuric acid at a maximum temperature of 35° C. At a temperature from 25 to 28° C., 104 parts of 40% nitrosylsulfuric acid are then added dropwise over 40 minutes to the reaction mixture which is then stirred for 120 minutes at 25° C. The resulting diazo solution is then added dropwise over 60 minutes at 0 to 5° C. to 300 parts of the 35% solution of the coupling component of Example 1 and to 200 parts of ice, the reaction temperature being kept at a maximum of 5° C. by addition of ice. After the addition of the diazo solution is complete, the mixture is stirred for 2 hours, the temperature rising to 20° C. The resulting precipitate is collected by filtration, washed with water and dried, giving 153 parts of a dye of formula

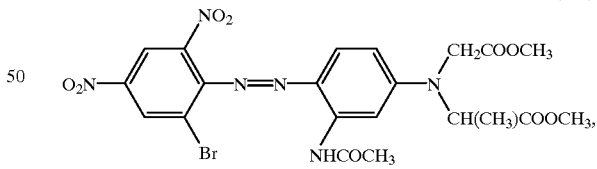

(101)

having an absorption maximum $\lambda_{max}$ at 516 nm. This dye dyes polyester textile material in a red to violet shade having good fastness properties.

EXAMPLES 3–27

In analogy to the instructions of Examples 1 and 2, it is possible to prepare the dyes of formulae (102) to (126) listed in Table 1 if, during the preparation of the coupling component according to Example 1, 50.0 parts of 3-aminoacetanilide are replaced by an equimolar amount of the compound of formula

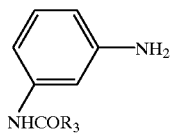

which is either reacted first with a compound of formula $CH_3$—CHCl—$COOR_5$ and then with a compound of formula Cl—$CH_2$—$COOR_4$ or which is alkylated completely with the compounds of formulae Cl—$CH_2$—$COOR_4$ and Cl—$CH_2$—$COOR_5$, wherein $R_4$ and $R_5$ are identical or different, and if, during the diazotisation and coupling according to Example 2, 78.6 parts of 2-bromo-4,6-dinitroaniline are replaced by an equimolar amount of the compound of formula

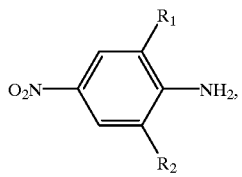

wherein $R_1$, $R_2$, $R_3$, $R_4$, and $R_5$ have the meanings cited in Table 1 for the respective dyes.

TABLE 1

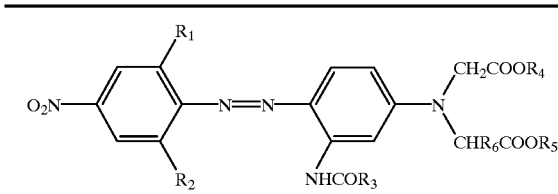

| Ex. No./ formula No. | $R_1$ | $R_2$ | $R_3$ | $R_4$ | $R_5$ | $R_6$ | $\lambda_{max}$ [nm] |
|---|---|---|---|---|---|---|---|
| 3/(102) | $NO_2$ | Cl | $CH_2CH_3$ | $CH_3$ | $CH_2CH_3$ | H | 520 |
| 4/(103) | $NO_2$ | Br | $CH_2CH_3$ | $CH_3$ | $CH_2CH_3$ | H | 516 |
| 5/(104) | $NO_2$ | Br | $CH_2CH_3$ | $CH_2CH_3$ | $CH_2CH_3$ | H | 516 |
| 6/(105) | $NO_2$ | Br | $CH_3$ | $CH_2CH_3$ | $CH_3$ | $CH_3$ | 516 |
| 7/(106) | $NO_2$ | Br | $CH_3$ | $CH_3$ | $CH_2CH_3$ | $CH_3$ | 516 |
| 8/(107) | $NO_2$ | Br | $CH_3$ | $CH_2CH_3$ | $CH_2CH_3$ | $CH_3$ | 516 |
| 9/(108) | $NO_2$ | Cl | $CH_2CH_3$ | $CH_3$ | $CH_3$ | H | 521 |
| 10/(109) | $NO_2$ | Cl | $CH_2CH_3$ | $CH_2CH_3$ | $CH_2CH_3$ | H | 520 |
| 11/(110) | $NO_2$ | Cl | $CH_3$ | $CH_3$ | $CH_3$ | $CH_3$ | 519 |
| 12/(111) | $NO_2$ | Cl | $CH_3$ | $CH_3$ | $CH_2CH_3$ | $CH_3$ | 521 |
| 13/(112) | $NO_2$ | Cl | $CH_3$ | $CH_2CH_3$ | $CH_3$ | $CH_3$ | 519 |
| 14/(113) | $NO_2$ | Cl | $CH_3$ | $CH_2CH_3$ | $CH_2CH_3$ | $CH_3$ | 520 |
| 15/(114) | CN | Br | $CH_2CH_3$ | $CH_3$ | $CH_3$ | H | 544 |
| 16/(115) | CN | Br | $CH_2CH_3$ | $CH_2CH_3$ | $CH_2CH_3$ | H | 546 |
| 17/(116) | CN | Br | $CH_3$ | $CH_3$ | $CH_3$ | $CH_3$ | 544 |
| 18/(117) | CN | Br | $CH_3$ | $CH_3$ | $CH_2CH_3$ | $CH_3$ | 545 |
| 19/(118) | CN | Br | $CH_3$ | $CH_2CH_3$ | $CH_3$ | $CH_3$ | 544 |
| 20/(119) | CN | Br | $CH_3$ | $CH_2CH_3$ | $CH_2CH_3$ | $CH_3$ | 544 |
| 21/(120) | CN | Cl | $CH_2CH_3$ | $CH_3$ | $CH_3$ | H | 547 |
| 22/(121) | CN | Cl | $CH_2CH_3$ | $CH_3$ | $CH_3$ | H | 544 |
| 23/(122) | CN | Cl | $CH_2CH_3$ | $CH_2CH_3$ | $CH_2CH_3$ | H | 545 |
| 24/(123) | CN | Cl | $CH_3$ | $CH_3$ | $CH_3$ | $CH_3$ | 544 |
| 25/(124) | CN | Cl | $CH_3$ | $CH_3$ | $CH_3$ | $CH_3$ | 546 |
| 26/(125) | CN | Cl | $CH_3$ | $CH_3$ | $CH_2CH_3$ | $CH_3$ | 544 |
| 27/(126) | CN | Cl | $CH_3$ | $CH_2CH_3$ | $CH_2CH_3$ | $CH_3$ | 544 |

The dyes listed in Table 1 likewise dye the polyester textile material in a violet shade having good fastness properties.

What is claimed is:

1. A dye of formula

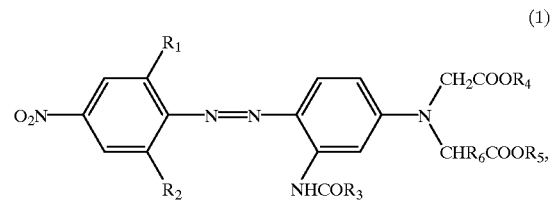

wherein $R_1$ is nitro or cyano, $R_2$ is halogen, $R_3$ is $C_1$–$C_4$alkyl, $R_4$ and $R_5$ are each independently of the other methyl or ethyl and $R_6$ is methyl or ethyl.

2. A dye according to claim 1, wherein $R_2$ is chloro or bromo.

3. A dye according to claim 2, wherein $R_2$ is bromo.

4. A dye according to claim 1, wherein $R_3$ is $C_1$–$C_3$alkyl.

5. A dye according to claim 1, wherein $R_6$ is methyl.

6. A dye according to claim 1, wherein $R_1$ is cyano, $R_2$ is chloro or bromo, $R_3$ is $C_1$–$C_3$alkyl, $R_4$ and $R_5$ are each independently of the other methyl or ethyl and $R_6$ is methyl.

7. A dye according to claim 1, wherein $R_1$ is cyano, $R_2$ is chloro or bromo and $R_3$, $R_4$, $R_5$ and $R_6$ are methyl.

8. A process for the preparation of a dye of formula (1) according to claim 1, which comprises diazotising a compound of formula

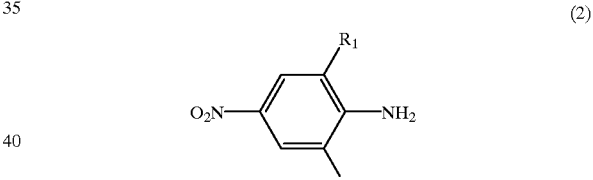

and coupling the diazonium compound so obtained to a coupling component of formula

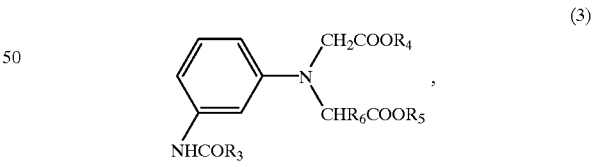

wherein $R_1$ is nitro or cyano, $R_2$ is halogen, $R_3$ is $C_1$–$C_4$alkyl, $R_4$ and $R_5$ are each independently of the other methyl or ethyl and $R_6$ is is methyl or ethyl.

9. A process for dyeing or printing semisynthetic or synthetic hydrophobic fibre material, which comprises applying to, or incorporating into, the cited material one or more than one dye according to claim 1.

10. A process according to claim 9, wherein the hydrophobic material consists of polyester fibres.

11. A coupling component of formula

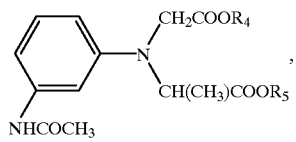

(3a)

wherein $R_4$ and $R_5$ are each independently of the other methyl or ethyl.

12. A process for the preparation of the coupling component of formula (3a) according to claim 11, which comprises reacting 3-aminoacetanilide first with a compound of formula $CH_3$—$CHCl$—$COOR_5$ and then with a compound of formula $Cl$—$CH_2$—$COOR_4$ wherein $R_4$ and $R_5$ are each independently of the other methyl or ethyl.

* * * * *